US006486144B1

(12) United States Patent
Morris

(10) Patent No.: US 6,486,144 B1
(45) Date of Patent: Nov. 26, 2002

(54) METHOD OF TREATMENT OF LIVER TUMORS AND PHARMACEUTICAL COMPOSITIONS FOR USE THEREIN

(75) Inventor: David Lawson Morris, New South Wales (AU)

(73) Assignee: MRC Holdings Pty Limited, New South Wales (AU)

( * ) Notice: Subject to any disclaimer, the term of this patent is extended or adjusted under 35 U.S.C. 154(b) by 0 days.

(21) Appl. No.: 09/445,688

(22) PCT Filed: Jun. 10, 1998

(86) PCT No.: PCT/AU98/00440

§ 371 (c)(1),
(2), (4) Date: Jan. 20, 2000

(87) PCT Pub. No.: WO98/56387

PCT Pub. Date: Dec. 17, 1998

(30) Foreign Application Priority Data

Jun. 10, 1997 (AU) ............................................. PO7270

(51) Int. Cl.$^7$ ............................................. A61K 31/59
(52) U.S. Cl. ..................................................... 514/167
(58) Field of Search ........................................ 514/167

(56) References Cited

U.S. PATENT DOCUMENTS

| 4,897,387 A | | 1/1990 | Ikekawa et al. | |
| 4,927,815 A | * | 5/1990 | DeLuca et al. | ............. 514/167 |
| 5,856,189 A | * | 1/1999 | Watkins et al. | ............. 435/375 |

FOREIGN PATENT DOCUMENTS

| EP | 0 296 800 | 12/1988 |
| EP | 0 296 800 A1 | 12/1988 |
| WO | 95/01960 | 1/1995 |
| WO | 95/010960 | 1/1995 |
| WO | 95/40153 | 12/1996 |
| WO | 96/40153 | 12/1996 |

OTHER PUBLICATIONS

Dalhoff et al.; Seocalcitol (EB 1089) . . . Carcinoma; Hepatolgy; vol. 28(4); pp227A, 1999.*
Abe et al, "A Novel Vitamin $D_3$ Analog, 22–Oxa–1,25–Dihydroxyvitamin . . . ," Endocrinology, vol. 129, No. 2, pp. 832–837 (1991).
Abe–Hashimoto et al, "Antitumor Effect of 22–Oxa–calcitriol, a Non–calcemic . . . ," Cancer Research, vol. 53, No. 11, pp. 2534–2537 (1993).
Kanematsu, M., "Transcatheter arterial chemoembolization therapy with . . . ," Journal of Gastroenterology, vol. 30, pp. 215–223 (1995).
Habener, et al, "Osteomalacia and Disorders..," Ann. Rev., Med., vol. 29, pp. 327–342 (1978).
Dilworth et al., "The Vitamin D. Analog," Endocrinology, vol. 138, No. 12, pp. 5485–5496.
Cremoux et al, "1,25–dihydroxycholecalciferol,"Fundam. Cliin. Pharmacol., vol. 1, pp. 347–356 (1987).
Jones et al, "A Dialogue on Analogues," TEM, vol. 4, No. 9, pp. 297–303 (1993).
Martindale—The Extra Pharmacopoeia, 13$^{th}$ Ed. (1993).
The Pharmacological Basis of Therpeutics, vol. II (1992).
Choi, J., "Regional Transcatheter Therapy of Hepatic Neoplasms," Cancer Control: Journal of the Moffitt Cancer Center, vol. 3, No. 5, pp. 407–413 (1996).
Pols et al, "Vitamin D: A Modulator of Cell Proliferation and Differentiation," J. Steroid Biochem. Molec. Biol., vol. 37, No. 6, pp. 873–876 (1990).
DeLuca, O., "The relationship between the . . . ," Adv. Exp. Med. Biol., vol. 206, pp. 413–429 (1986).
Tanaka et al, "1,25–dihydroxyvitamin $D_3$–induced . . . ," Biochem. Pharm., vol. 38, No. 3, pp. 449–453 (1989).
Hamada et al, "Novel vitamin $D^3$ analog . . . ," Drugs of the Future, vol. 18, No. 11, pp. 1057–1061 (1993).
Martin, L., "Current Treatment Modalities for . . . ," Annals of Surgery, vol. 219, No. 3, pp. 236–247 (1994).
Takeuchi et al, "The enzymatic formation of 1α,25–dihydroxyvitamin . . . ," Comp. Biochem. Physical, vol. 109C, No. 1, pp. 1–7 (1994).
Strungnell et al, "1α,25(S)–Dihydroxyvitamin . . . ," pp. 233–241 (1995).
Wijngaarden et al, "Inhibition of breast cancer . . . ," Cancer Research, vol. 54, pp. 5711–5717 (1994).
Jiang et al, "Tamaoxifen inhibits hepatoma cell growth . . . ," Journal of Hepatology, vol. 23, pp. 712–719 (1995).
Love–Schimenti et al, "Anteestrogen Potentiation of Antiproliferative Effect . . . ," J. Cancer Research, vol. 56, pp. 2789–2974 (1996).
Sakai et al, "Study on 1,25–dihydroxyvitamin . . . ," Acta Hepatol Jpn, vol. 29, No. 12, p. 1618 (1988).
Sato et al, "Effects of 1α–hydroxyvitamin . . . ,"Br. J. Cancer, vol. 50, pp. 123–125 (1984).
Clinical Research, vol. 39, No. 2 (1991).
Habener et al, "Osteomalacia and Disorders of Vitamin D Metabolism," Ann. Rev. Med., vol. 29, pp. 327–342 (1978).
Dilworth et al, "The Vitamin D Analog, KH1060, Is Rapidly Degraded . . . ," Endocrinology, vol. 138, No. 12, pp. 5485–5496 (1997).
Cremoux et al, "1,25–dihydroxycholecalciferol induces an increase in $PGE_1$ and . . . " Fundam. Clin. Pharmacol, vol. 1, pp. 347–356 (1987).
Jones et al, "A Dialogue on Analogues: Newer Vitamin–D Drugs . . . ," TEM, vol. 4, No. 9, pp. 297–303 (1993).
Martindale, The Extra Pharmacopoeia, 13$^{th}$ ed., 1993, pp. 1038, 1058, 1059, 1060, 1061.

* cited by examiner

Primary Examiner—Theodore J. Criares
(74) Attorney, Agent, or Firm—Nixon & Vanderhye

(57) ABSTRACT

Method for the treatment of tumors in the liver of a subject wherein a pharmaceutically effective amount of at least one vitamin D compound selected from vitamin D, a precursor of vitamin D or a metabolite or analog thereof, is administered to the subject. The method involves regional delivery of the vitamin D compound to the liver, for example by intraarterial infusion to the hepatic artery. Compositions are also provided for use in such treatment.

18 Claims, 12 Drawing Sheets

Figure 3. Patient 4 Serum calcium levels

Figure 4. Patient 7 Serum calcium levels

Figure 6. All Patients Serum calcium levels

Figure 7. Patient 5 Serum calcium levels

Figure 8. Patients 1 – 4 CEA levels

Figure 9. CEA levels of Patients 5-7

Figure 10. Pig one - calcium levels for intravenous and hepatic artery infusion

Figure 11. Pig two - calcium levels for intravenous and hepatic artery infusions 100 uL Lipiodol + 100uL Water
Cold vitamin $D_3$ in Lipiodol 4mM

METHOD OF TREATMENT OF LIVER TUMORS AND PHARMACEUTICAL COMPOSITIONS FOR USE THEREIN

The present invention is concerned with a method for the treatment of tumours and in particular, with a method for the treatment of tumours in the liver. The invention is also concerned with compositions suitable for such treatment.

BACKGROUND OF THE INVENTION

Hepatoma (primary liver cancer) is one of the commonest causes of cancer death in the world with an estimated incidence of 1 million cases per year worldwide (Lencioni R and Bartolozzi C. The Cancer Journal, Vol 10, pp1–6). There is a considerable variation in its incidence with it being the most common in Asian countries. although it is now of increasing importance in the West. There are currently few effective treatment options available. Untreated, the average survival in this condition is of the order of 3 months. Liver resection may allow 5 year survival in approximately 40% of cases but very few patients are eligible for such treatment. Systemic chemotherapy has been of very limited value in the treatment of primary hepatic cancer, and attempts have consequently been made to deliver pharmacologically active agents directly to the liver using the technique of transarterial chemoembolisation (TAE). TAE combines the selective delivery of agents to hepatic tumours vascularized by the hepatic artery and thus their concentration in the tumour, with the concept of causing embolisation of the tumour and hence necrosis by ischemia. A wide range of chemotherapy agents have been delivered in this way, including doxorubicin, epirubicin and cisplatin (Choi, J. Cancer Control, Vol 3, pp407–413, 1996). Frequently, chemotherapeutic agents are emulsified with or dissolved in the contrast agent Lipiodol, which is an iodised poppy seed oil fatty acid ethylester. Uptake of iodised oil into tumours is thought to prolong contact of the chemotherapeutic agent with tumour, and the radioopaque nature of the medium enables progress of the infusion to be monitored by radiography.

Vitamin D is an isoprenoid compound made up of activated 5-carbon units. The most abundant form of vitamin D is vitamin $D_3$, or cholecalciferol. Vitamin $D_3$ arises from biosynthesis of 7-dehydrocholesterol, an intermediate in cholesterol biosynthesis. Vitamin $D_3$ is metabolised in the liver to 25-hydroxycholocalciferol [$25(OH)D_3$] which is a major form of Vitamin D circulating in the blood compartment. $25(OH)D_3$ is converted by the kidney to produce two principal dihydroxylated metabolites, namely, 1.25-dihydroxycholecalciferol [$1.25(OH)_2D_3$] and 24,25-dihydroxycholocalciferol [$24R,25(OH)_2D_3$].

$1.25(OH)_2D_3$ is the most biologically active naturally occurring form of vitamin $D_3$ and is transported in the bloodstream to its major site of action in the mucosal cells of the intestine, where calcium absorption is stimulated. Thus vitamin $D_3$ may be regarded as a prohormone because it is converted to a metabolite that acts analogously to a steroid hormone. It regulates calcium and phosphorous metabolism particularly in the synthesis of the inorganic matrix of bones.

Therapeutically, $1.25(OH)_2D_3$ and certain other analogues of Vitamin $D_3$ are used to counteract deleterious effects of dietary deficiency of Vitamin D (rickets), or in the treatment of diseases characterised by abnormalities in the synthesis of or response to Vitamin D such as hypophosphatemic vitamin D-resistant rickets and renal osteodystrophy (renal rickets). A further use in the calcification-related disease osteoporosis is distinct from assuring vitamin D nutritional adequacy. Here, the rationale is directly to suppress parathyroid function and reduce bone turnover (Goodman & Gilman, The Pharmacological basis of Therapeutics. Pub. 1992, The McGraw Hill Companies Inc). Finally, a recent use of Vitamin $D_3$ analogues is in the treatment of the cutaneous disease psoriasis.

Experimental studies have shown that Vitamin $D_3$ receptors are present on a range of cell types and so the understanding has arisen that the Vitamin D endocrine system is involved in the modulation of a number of fundamental cellular processes not directly related to calcium homeostasis (Pols, HAP et al, J Steroid Biochemistry, Vol 37, pp873–876, 1990). Included amongst the cells bearing Vitamin $D_3$ receptors are a number of malignant tissues or cell lines derived from tumours. The presence of receptors on some cancer cells has been shown to have a functional significance in a number of cases, and the literature contains reports of Vitamin $D_3$ and analogues being able to inhibit the proliferation of melanoma, osteosarcoma and breast carcinoma cells (Deluca HF and Ostrem V, Advances in Experimental Medicine and Biology, Vol 206, pp413–429, 1986) colon adenocarcinoma cells (Cross HS et al Journal of Nutrition, Vol 127 Suppl. pp2004–2008, 1995) and hepatic tumour cells (Tanaka Y et al, Biochem Pharmacol vol 38 pp449–453, 1989).

This effect in vitro has given rise to the hope that Vitamin $D_3$ and analogues could be used in the treatment of cancers. Vitamin $D_3$ compounds are listed among "unconventional cancer therapies" (British Columbia Cancer Agency publication; 600 West 10th Ave, Vancouver, BC, Canada), and clinical trials have attempted to show an effect. Unfortunately, attempts to use naturally occurring analogues of Vitamin $D_3$ such as $1.25(OH)_2D_3$ have not been associated with the successful treatment of cancer and indeed have rarely been attempted. This is due in large part to the observation that for growth reduction of cancer cells to be caused by Vitamin $D_3$, supraphysiological concentrations are needed (Pols et al-ibid). The consequence of this is that before anti-tumour properties of the treatment can be expressed, the effects of Vitamin $D_3$ on calcium homeostasis are expressed to an excessive and dangerous degree, leading to life-threatening toxicity from hypercalcaemia.

In an attempt to overcome this problem, and to disassociate the hypercalcaemic effect of Vitamin $D_3$ from its actions on cell differentiation, the pharmaceutical industry has expended much effort on the search for synthetic analogues that are devoid of an effect on calcium metabolism, and might therefore be useful for the treatment of cancer or other diseases. This approach has met with some limited success. For example, the analogue Calcipotriol has been synthesized which contains a 22–23 double bond, a 24(S)-hydroxy functional group, and carbons 25–27 incorporated into a cyclopropane ring. This compound has receptor affinity similar to that of $1.25(OH)_2D_3$, but it is less than 1% as active as $1.25(OH)_2D_3$ in regulating calcium metabolism. Calcipotriol has been studied extensively as a potential treatment for psoriasis (Goodman & Gilman, The Pharmacological Basis of Therapeutics Pub McGraw Hill, 1992). However, despite its reduced effect on calcium metabolism, calcitriol is used topically in order to avoid systemic hypercalcaemia. Examples have also been disclosed of synthetic Vitamin D analogues claimed to be useful for the treatment of tumours which have reduced effects on calcium metabolism (U.S. Pat. No. 4,891,364, Jan 2 1990). Also, attempts have been made to treat certain cancers locally. Thus, Bower M et al treated breast cancer topically with Calcipotriol (Lancet vol 337: No 8743 pp701–702). Of the 19 patients treated, only 3 showed a significant response and 1 a minimal response. Moreover, even though this synthetic analogue has a drastically reduced effect on calcium metabolism (vide supra) and even though the treatment was locally restricted to skin around breast cancer lesions, still 2 of the 19 patients became hypercalcaemic during treatment.

Thus, despite the interesting findings of basic researchers and the intensive efforts of the pharmaceutical industry, the application of Vitamin D compounds to cancer therapy has not been successful. The key limitation has been either an inherent lack of activity, or the low therapeutic index (ratio of effective dose to toxic dose) of Vitamin $D_3$ which has made its use so difficult.

SUMMARY OF THE INVENTION

We have found that, surprisingly, regional delivery to the liver of a vitamin D compound, such as vitamin $D_3$ or a precursor, metabolite or analogue thereof, avoids the production of hypercalcaemia, even at high doses of the vitamin D compound. For example, despite the fact that therapeutic oral and intravenous doses of $1.25(OH)_2D_3$ are typically in the order of 0.5 to 3 mcg/day (at or beyond which level there is a distinct risk of hypercalcaemia developing), we have shown (Example 2) that doses of at least 10 mcg/day can be administered intraarterially to the liver without any observable systemic toxicity.

A reasonable conclusion of this observation is that the avoidance of hypercalcaemia after such high doses of Vitamin D compound is due to increased retention of the Vitamin D compound in the liver, or degradation in the liver (a first pass effect). However, neither of these occurrences could have been predicted for the following reasons: The dose provided is much higher than physiological levels, and thus, although arterial infusion would bring the Vitamin D compound into contact with cells bearing Vitamin D receptors, they would not be expected to be capable of trapping all the Vitamin D compound. Concerning degradation, the major metabolic activity of the liver is applied to compounds entering via the hepatic portal route, not the hepatic artery. Moreover, as was discussed above, the liver is one of the sites of activation of Vitamin D and would not necessarily be expected to remove Vitamin D compounds from the blood. The precise reasons why the Vitamin D compound induce less hypercalcaemia after hepatic arterial delivery are not known.

Regional delivery of Vitamin $D_3$ to the liver has not only been shown to be safe, but in 4 of 7 patients had at least a limited response to treatment as indicated by changes in their rate of rise of tumour marker.

Thus, not only has the surprising ability to administer large doses of Vitamin D compound to the liver by regional delivery been demonstrated, but also indications of a beneficial effect on disease progress have been obtained.

Accordingly, the first aspect of the present invention consists in a method of treating a tumour in the liver of a subject including administering to the subject a pharmaceutically effective amount of at least one vitamin D compound selected from the group consisting of vitamin D, a precursor of vitamin D, or a metabolite or analogue thereof, wherein the vitamin D compound is regionally delivered to the liver.

The regional delivery of the vitamin D compound may be achieved by intraarterial delivery or delivery via the portal vein. Preferably the vitamin D compound is delivered intraarterially. Particularly preferred is where the vitamin D compound is delivered by intraarterial infusion via the hepatic artery.

The method of treatment of the invention may be used to treat primary or secondary cancers of the liver. The method of the invention is particularly suitable for the treatment of hepatoma (primary liver cancer) in a subject. The method of the invention may also be used to treat secondary cancers in the form of metastases in the liver, for example, metastases of colorectal cancer, lung cancer, breast cancer, prostate cancer, pancreatic cancer or renal cancer. The secondary cancer may be a sarcoma. The method of the invention may be used to treat primary or secondary liver cancers in the liver.

Preferably the vitamin D compound is vitamin $D_3$ or a precursor or metabolite thereof, although the vitamin D compound may be an analogue of vitamin $D_3$.

The vitamin D analogue compound may be selected from any suitable analogue, for example, $1.25(OH)_2D_3$ (1-25-dihydroxycholecalciferol), OCT (22-Oxacalcitirol), MC903 (calcipotriol) or EB1089 (1 α.25 $(OH)_2$ 22.24 diene 24.26.27 trihomo $D_3$).

The metabolite of vitamin D may be a hydroxylated or other product of vitamin D or its analogues.

The effect of the vitamin D compound on tumours is very dose dependent and there is therefore advantage in delivering high concentrations of the vitamin D compound to the tumour. However, the limited solubility of vitamin D compounds in a conventional carrier such as aqueous media places an upper limit on the amount of compound that can be delivered to the tumour.

We have found that very high concentrations of a vitamin D compound, such as $1.25(OH)_2D_3$, can be achieved by dissolving the compound in a pharmaceutically acceptable oil. For example, 2 mg of $1.25(OH)_2D_3$ can be readily dissolved in 1 ml lipiodol. This high solubility allows for very high concentrations of vitamin D compound to the tumour. A further advantage of using an oil as the carrier for the vitamin D compound is that some oils are concentrated in certain tumours allowing the achievement of very high tumour concentrations of the vitamin D compound. Moreover, another advantage of achievement of high concentrations is that some vitamin D compounds that are inactive at low concentrations may become active at the much higher concentrations achieved when an oil is used to dissolve the compound.

Accordingly, in a second aspect the present invention consists in a method of treatment of the first aspect wherein the vitamin D is delivered as a solution of the vitamin D compound in a pharmaceutically acceptable oil.

The oil may be an iodised oil such as lipiodol although clearly the presence of iodine, while possibly being useful to allow infusion to be monitored radiographically, is not an essential feature of the oily agent. Furthermore, the oily agent needs only to (1) incorporate large amounts of Vitamin D compound and (2), if possible, be taken up into tumours being treated. Therefore, to one skilled in the art, the carrier could also be deemed to include other oils and chemically modified oils used in the pharmaceutical industry such as Cremophor (polyoxyethylated castor oil). Examples of oils for intra-arterial tumour treatment are disclosed in U.S. Pat. No. 4,578,391, which disclosure however is solely concerned with the dissolution of sparingly oil-soluble or water soluble anti-tumour drugs for infusion. Known formulations for intravenous use (Calcijex® calcitriol injection marketed by Abbot Laboratories, as described in the Physicians Desk Reference, ibid, and also formulations disclosed in U.S. Pat. No. 4,308,264) are aqueous solutions and their use in the treatment of cancers has not been reported. Moreover, their low calcitriol content would make them particularly unsuited to intra-arterial administration to the liver.

Further suitable carriers include multicomponent systems capable of incorporating lipophilic materials such as liposomes and microemulsions.

Tamoxifen, an oestrogen receptor antagonist, has been shown to significantly, but modestly, improve survival in human hepatoma. It has also been shown that tamoxifen increases vitamin D receptor expression on breast cancer lines. We believe that tamoxifen's effect on hepatoma may be due to its effect on vitamin D receptor expression, making the tumour more sensitive to endogenous vitamin D. Tamoxifen and oestrogen or oestrogen-like compounds are therefore expected to significantly increase the effect of vitamin D therapies in cancers such as hepatoma and that this will significantly increase response whilst allowing lower doses of the vitamin D compound, thus avoiding hypercalcaemia and other complications.

Accordingly in a third aspect, the present invention consists in a method of treatment in accordance with the first and second aspects of the invention, the method further including administration of a compound capable of increasing vitamin D receptor expression is also administered.

The compound capable of increasing vitamin D receptor expression may be tamoxifen or other oestrogen or oestrogen-like compound.

The compound capable of increasing vitamin D receptor expression may be administered before, concurrently or after administration of the vitamin D compound.

In a fourth aspect the present invention consists in a composition suitable for the treatment of a tumour in the liver, the composition including a pharmaceutically effective amount of a vitamin D compound selected from the group consisting of vitamin D, a precursor of vitamin D, or a metabolite or analogue thereof dissolved in a pharmaceutically acceptable oil.

The pharmaceutically acceptable oil is an iodised oil such as iodised poppy seed oil. The pharmaceutically acceptable oil may be a non-iodised oil, for example, poppy seed oil.

EXAMPLES

In order that the invention be more readily understood, we provide the following non-limiting examples:

Example 1

Effect on in Vitro Growth of a Human Hepatoma Cell Line

Figure 1:
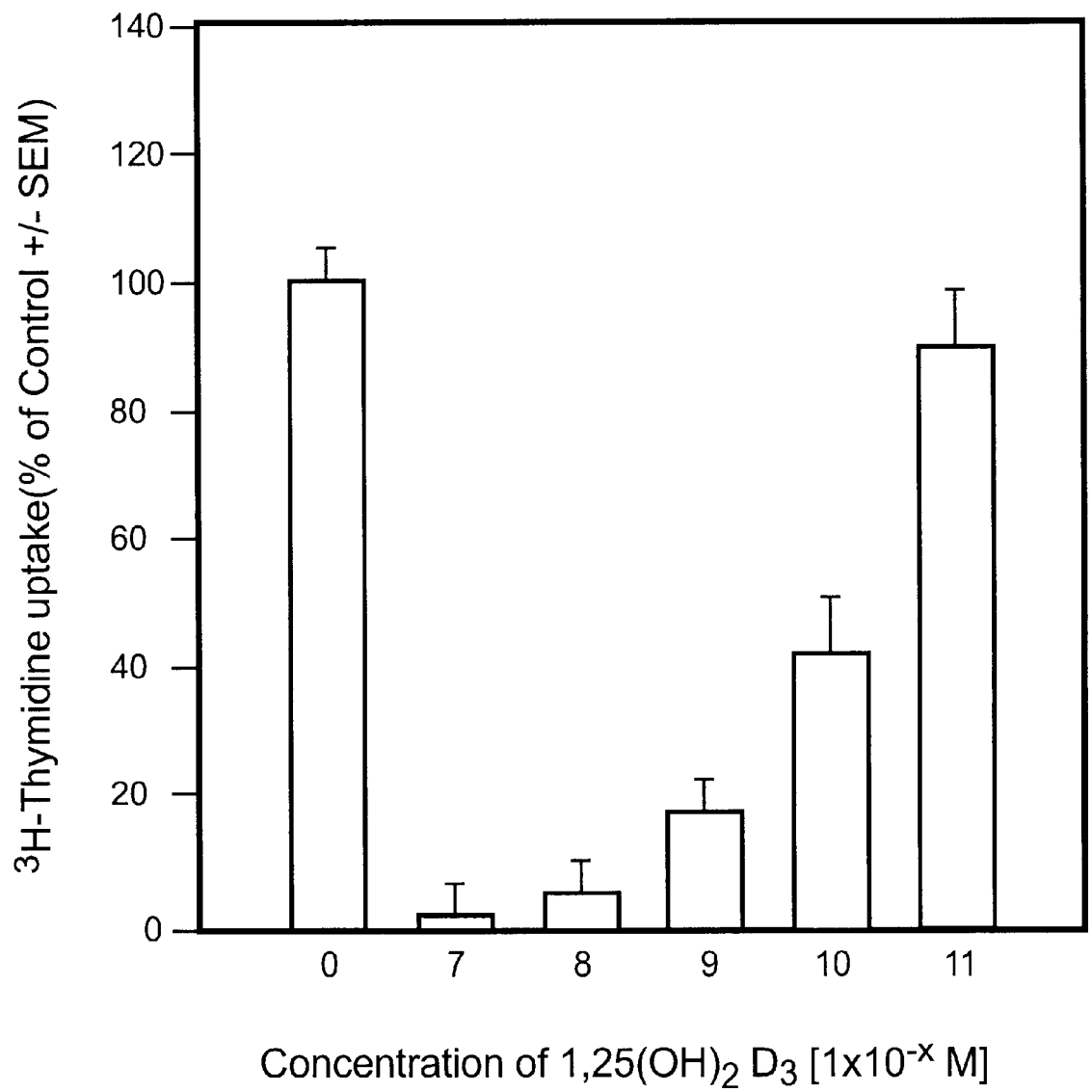
FIG. 1 is a graph showing the in vitro effect of 1.25 dihydroxyvitamin D3 on the growth of hepatoma HepG2 cells.

The effect of a range of concentrations of $1.25(OH)_2$ vitamin $D_3$ on the in vitro growth of the human hepatoma cell line, Hep G2, was studied. The inhibition of growth is demonstrated by a reduction in thymidine uptake by the hepatoma cells (see FIG. 1). The size of inhibition reported here is astonishing, a 95% inhibition of growth was seen, although this is dose dependent ($10^{-11}$M was considerably less effective). Whilst vitamin D analogues have been shown to inhibit other types of cancers, this is the first demonstration of effect in hepatoma.

Figure 2:
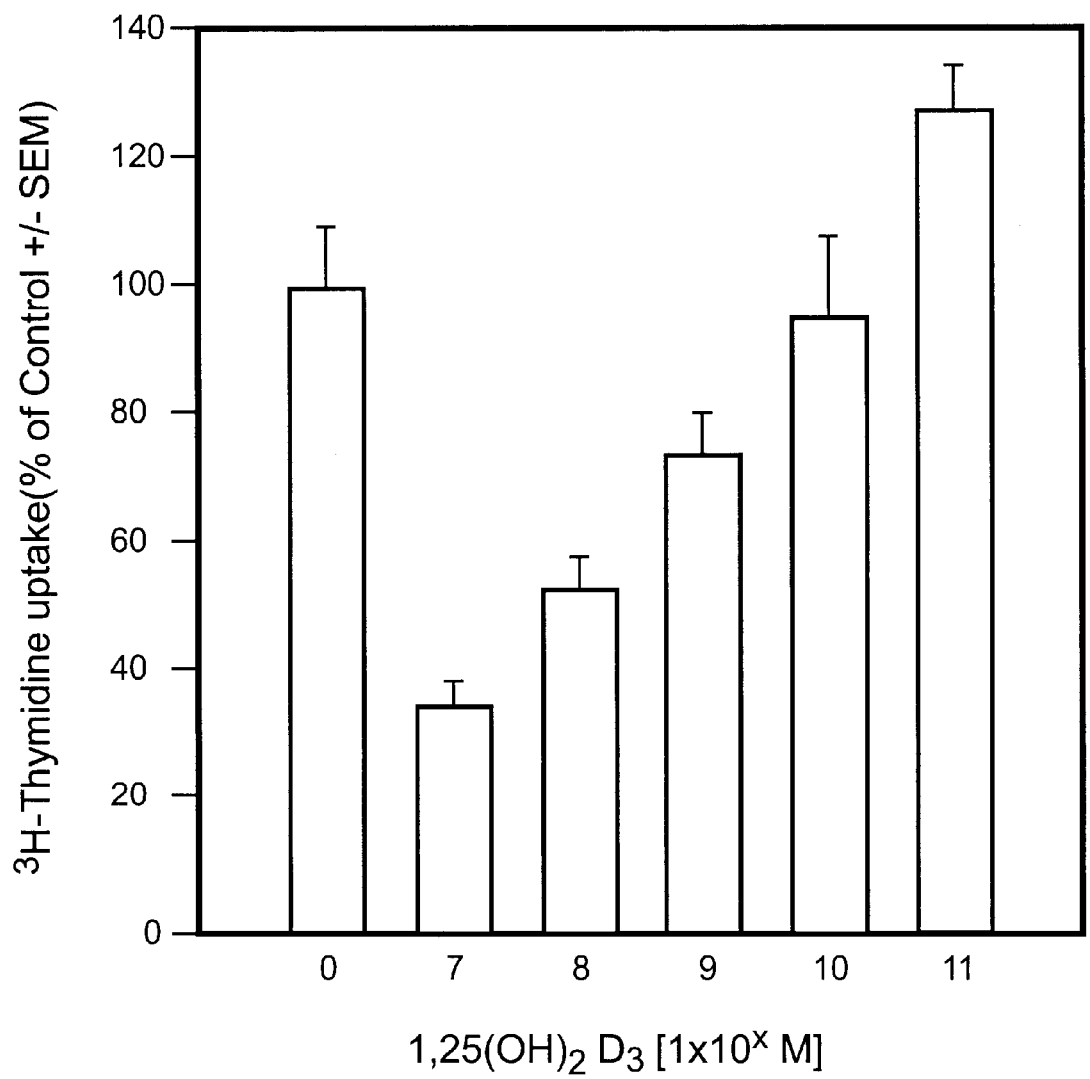
FIG. 2 is a graph showing the in vitro effect of 1.25 dihydroxyvitamin $D_3$ on the growth of human colon cancer cells LoVo treated for 10 days.

We have found that the size of the inhibition effect achieved with other cancers, for example, 50–60% inhibition of growth of colorectal cancer would be regarded as a good response (see FIG. 2). The effect of $1.25(OH)_2D_3$ would also be even less in colorectal cancer than the analogue (EB1089) used in this comparative experiment as set out in the table below.

Effect of $1.25(OH)_2D_3$ and EB1089 on human colon cancer cells LoVo and human hepatoma HepG2 cells. Results are % of control ±SEM

| | LoVo | | HepG2 | |
| --- | --- | --- | --- | --- |
| Concentration | $D_3$ | EB1089 | $D_3$ | EB1089 |
| $10^{-7}$ M | 34.2 ± 3.8 | 40.5 ± 10.7 | 7.1 ± 6.3 | 11.2 ± 2.7 |
| $10^{-8}$ M | 53.1 ± 5.0 | 51.0 ± 10.3 | 8.6 ± 6.3 | 13.1 ± 2.8 |
| $10^{-9}$ M | 74.2 ± 6.8 | 73.3 ± 11.7 | 13.8 ± 6.4 | 13.2 ± 2.7 |
| $10^{-10}$ M | 96.5 ± 12.9 | 55.3 ± 13.7 | 56.6 ± 6.7 | 49.1 ± 2.9 |
| $10^{-11}$ M | 127.4 ± 7.1 | 64.7 ± 12.7 | 105.6 ± 6.6 | 41.7 ± 3.6 |

LoVo cells were treated for 10 days, while HepG2 cells were treated for 5 days, with $D_3$ or EB1089.

The effect of vitamin $D_3$ analogue EB1089 on other hepatoma cell lines is given in the table below.

| | Concentration | | | | |
| --- | --- | --- | --- | --- | --- |
| Cell lines | $10^7$ M | $10^8$ M | $10^9$ M | $10^{10}$ M | $10^{11}$ M |
| SK-Hep | 34.8 ± 5.2 | 63.1 ± 16.2 | 52.1 ± 8.8 | 52.1 ± 8.6 | 82 ± 9.2 |
| | 46.6 ± 13.0 | 71.3 ± 11.8 | 61.6 ± 12.2 | 61.1 ± 16.6 | 78.8 ± 11.5 |
| | 79.2 ± 4.4 | 83.1 ± 4.2 | 88.4 ± 4.1 | 91.0 ± 4.5 | 118.3 ± 26.4 |
| | 60.1 ± 11.7 | 95.6 ± 12.2 | 103.1 ± 12.4 | 103.8 ± 11.7 | 66.9 ± 36.9 |
| Hep 1-6 | 56.1 ± 7.2 | 63.9 ± 7.0 | 78.1 ± 11.4 | 110.8 ± 13.8 | 103.4 ± 9.2 |
| | 118.9 ± 11.1 | 113.4 ± 5.6 | 106.7 ± 5.4 | 103.5 ± 4.5 | 98.1 ± 4.3 |
| HTC | 57.9 ± 7.2 | 63.9 ± 12.5 | 97.4 ± 13.8 | 107.8 ± 12.7 | 95.9 ± 13.0 |
| | 95.3 ± 17.7 | 86.9 ± 15.0 | 100.4 ± 15.4 | 113.0 ± 22.1 | 98.8 ± 15.5 |
| NovoKoff | 91.5 ± 14.5 | 106.0 ± 18.1 | 103.7 ± 13.8 | 116.3 ± 22.1 | 131.0 ± 15.9 |
| | 84.6 ± 17.0 | 79.0 ± 18.4 | 95.4 ± 18.2 | 94.0 ± 21.4 | 92.6 ± 17.6 |

-continued

| Cell lines | Concentration | | | | |
|---|---|---|---|---|---|
| | $10^7$ M | $10^8$ M | $10^9$ M | $10^{10}$ M | $10^{11}$ M |
| Morris | 136.0 ± 12.5 | 134.0 ± 13.3 | 117.8 ± 11.7 | 118.0 ± 11.9 | 118.0 ± 14.3 |
| | 80.1 ± 5.2 | 83.3 ± 4.7 | 79.1 ± 4.9 | 88.3 ± 3.9 | 90.8 ± 5.9 |
| PCL | 98.5 ± 4.5 | 101.6 ± 11.5 | 98.3 ± 6.5 | 92.5 ± 6.6 | 102.5 ± 10.0 |
| | 106.0 ± 9.1 | 105.2 ± 4.9 | 95.1 ± 3.3 | 100.1 ± 2.1 | 95.9 ± 2.9 |

(All experiments carried out in 5% charcoal treated media. All day 5. Successive lines of results for a particular cell line are the results for repeated experiment)

The speed of action is also very different, inhibition is measurable at 24 hours in hepatoma whereas results in colorectal cancer are modest at 5 days and usually only clear at 10 days.

The mechanism by which vitamin $D_3$ and its analogues achieve so much greater an effect in hepatoma from other cancers is, we believe, due to production of active metabolites by the hepatoma cells.

Example 2

Determination of First Pass Effect of $1.25(OH)_2D_3$

It is known that the principal route of excretion is in the bile, as calcitriolic acid and various other, conjugated compounds. We hypothesised that this catabolism in the liver would result in a first pass effect if $1.25(OH)_2D_3$ has been limited by high systemic concentrations and resultant hypercalcaemia.

Two trials were conducted with their aim being to determine whether such a first pass effect does exist, and is clinically useful. The trials were:

1. A phase one clinical trial looking at the effects of a hepatic artery infusion of $1.25(OH)D_3$.
2. A pig animal model comparing the effects of an intravenous administration of $1.25(OH)D_3$ versus an intravenous infusion. The methods and results of these trials are outlined below:

Phase 1 Trial

A phase one trial of the administration of a hepatic artery infusion of $1.25(OH)D_3$ was carried out.

Aims

1. To establish the safety of a hepatic artery infusion of $1.25(OH)D_3$ in the treatment of liver cancers, in particular its effects upon serum calcium levels.

2. To investigate the effects of such an infusion upon liver cancers by monitoring of tumour marker levels and their rate of rise.

Subjects:

Seven patients with either hepatoma or colorectal cancer metastases who have failed to respond to current chemotherapy regimens The subject details are given in the following table

| NUMBER | AGE | SEX | TUMOUR | EXTRAHEPATIC DISEASE/COMPLICATIONS |
|---|---|---|---|---|
| 1 | 62 | F | Colorectal | Lung Metastases |
| 2 | 73 | M | Hepatoma | Nil |
| 3 | 42 | M | Colorectal | Nil |
| 4 | 72 | F | Colorectal | Obstructive jaundice, partially relieved by indwelling stents |
| 5 | 5 7 | M | Colorectal | Nil |
| 6 | 75 | M | Colorectal | Lung Metastases, obstructive jaundice relieved by indwelling stents |
| 7 | 57 | M | Colorectal | Obstructive jaundice, partially relieved by indwelling stents |

The treatment summary is given in the following table

| Patient Number | Period 1 | | Period 2 | | Period 3 | | Period 4 | | Period 5 | |
|---|---|---|---|---|---|---|---|---|---|---|
| | Dose (mcg/day) | Days | Dose (mcg/day) | Days | Dose (mcg/day) | Days | Dose (mcg/day) | Days | Dose (mcg/day) | Days |
| 1 | 0.02 | 4 | 0.05 | 3 | | | | | | |
| 2 | 0.02 | 4 | 0.05 | 3 | | | | | | |
| 3 | 2 | 4 | 5 | 24 | 0 | 35 | 10 | 8 | 15 | 3 |
| 4 | 0.5 | 8 | 2 | 8 | 5 | 10 | | | | |
| 5 | 2 | 5 | 5 | 21 | 0 | 35 | 10 | 4 | 15 | 10 |
| 6 | 2 | 4 | 5 | 23 | 0 | 25 | 10 | 4 | 15 | 3 |
| 7 | 2 | 3 | 5 | 26 | | | | | | |

Methods

Each patient given an infusion of $1.25(OH)D_3$ via a hepatic artery catheter for either 1 week or successive 4 week periods. Regular assay of LFTs, UECs, and calcium and phosphate levels, together with AFP or CEA levels.

Patients 1 and 2 were given first 0.2 mcg/day of $1.25(OH)D_3$ or 4 days and were then given a further 3 days of 0.5 mcg/day, both via temporary hepatic artery catheters.

Patients 3, 5 and 6 were initially given 2 mcg/day, and then four weeks of 5 mcg/week. After a four week rest period in order to allow any induced hepatic enzymes to diminish they were restarted on treatment, at a dose of 10 mcg/day, this was quickly increased to 15 mcg/day.

Patient 4 was hypercalcaemic due to a paraneoplastic phenomena prior to treatment, and was therefore given lower dosages. Having started on 0.5 mcg/day this was quickly increased to 2 mcg/day and then to 5 mcg/day.

Patient 7 was commenced on the same dosage regimen as patients 3, 5 and 6 but was withdrawn from the trial prior to starting 10 mcg/day due to progression of his disease.

Outcome Measures

Calcium levels—looking for the development of hypercalcaemia

CEA or AFP levels—looking for evidence of response of the tumours to treatment

UECs and LFTs—looking for unexpected effects upon hepatic and renal function.

Results

Seven patients were entered in all. No patient suffered any unexpected adverse reaction or side effect to the infusion. Nor did any patient experience any derangement of hepatic or renal function.

Neither patients 1 nor 2 became hypercalcaemic during treatment (results not shown) with the lower doses.

Figure 3:
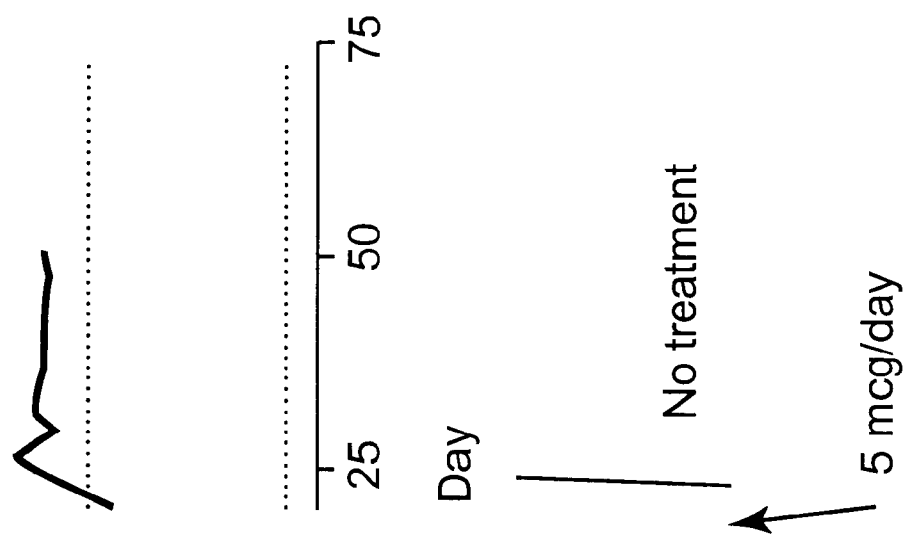
FIGS. 3–7 are charts showing patient serum calcium levels during treatment by the method in accordance with the present invention.

In FIG. 3 dotted lines denote normal range for serum calcium. Subjects 1 and 2 were treated from day 0 to 7. Subjects 3 to 7 were treated from 0 to 28.

Figure 4:
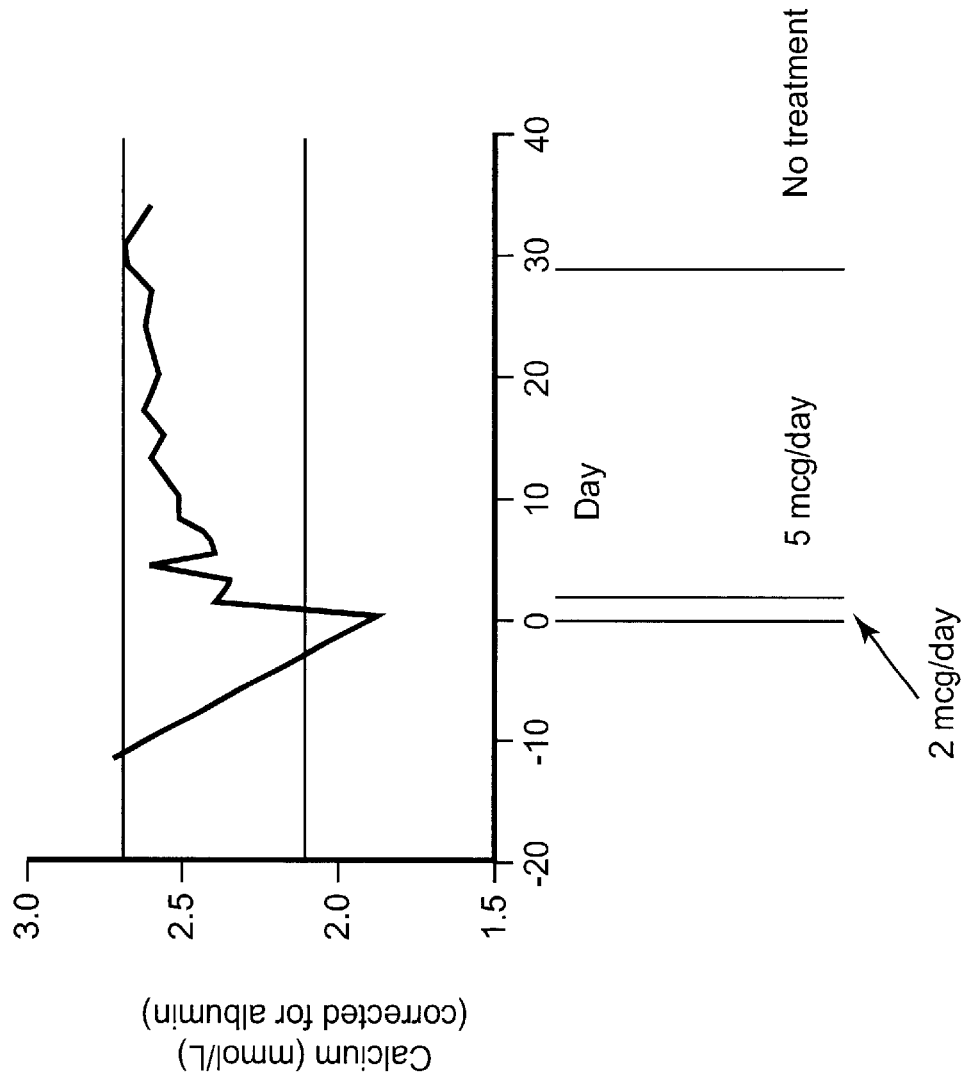

FIGS. 3 and 4 demonstrate that at hepatic arterial infusion of up to 5 mcg/day of 1.25(OH)$D_3$ do not result in hypercalcaemia. Indeed as demonstrated in FIG. 3, the calcium level of a patient with pre existing hypercalcaemia did not rise with treatment.

Figure 5:
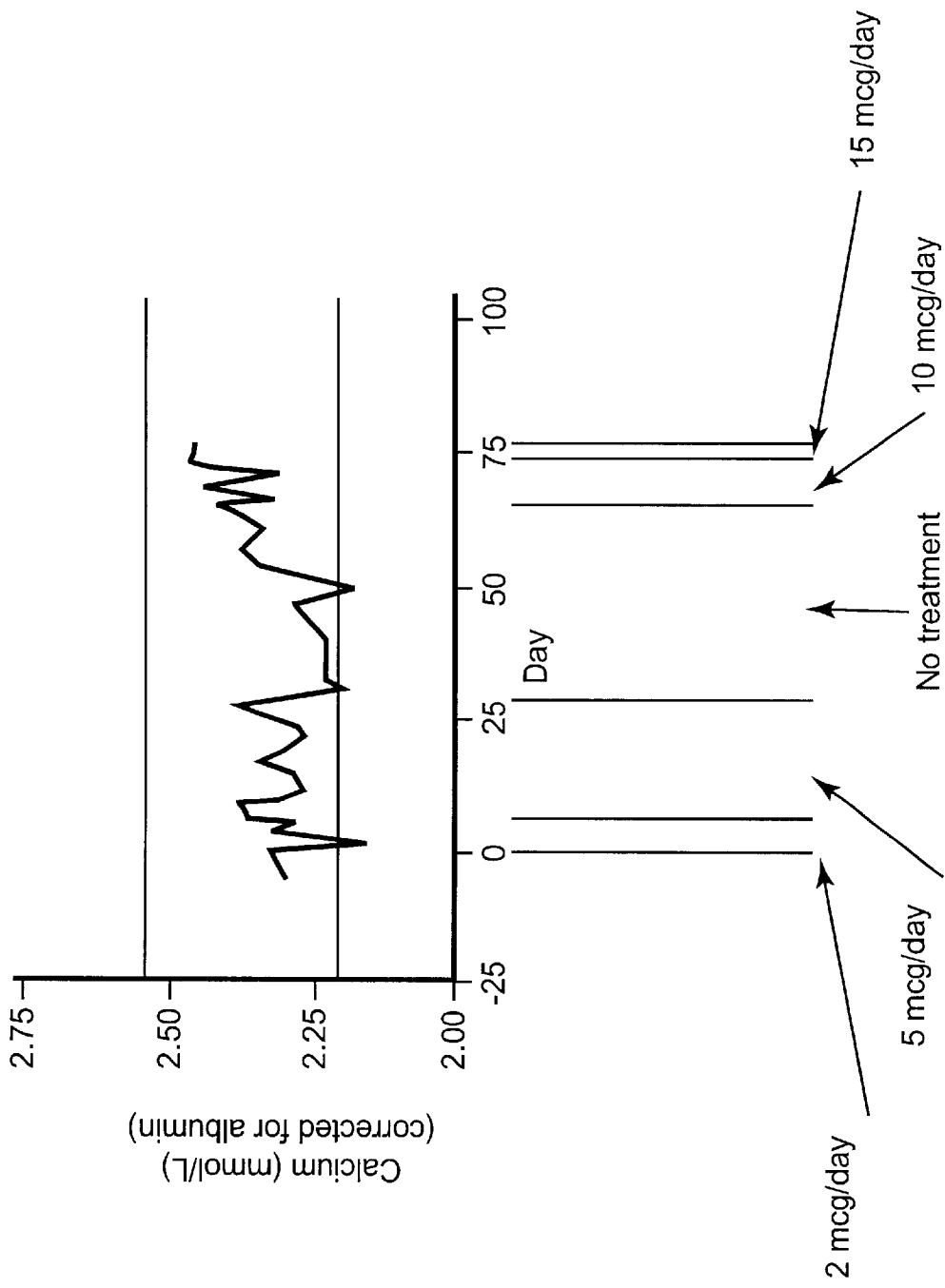
Figure 6:
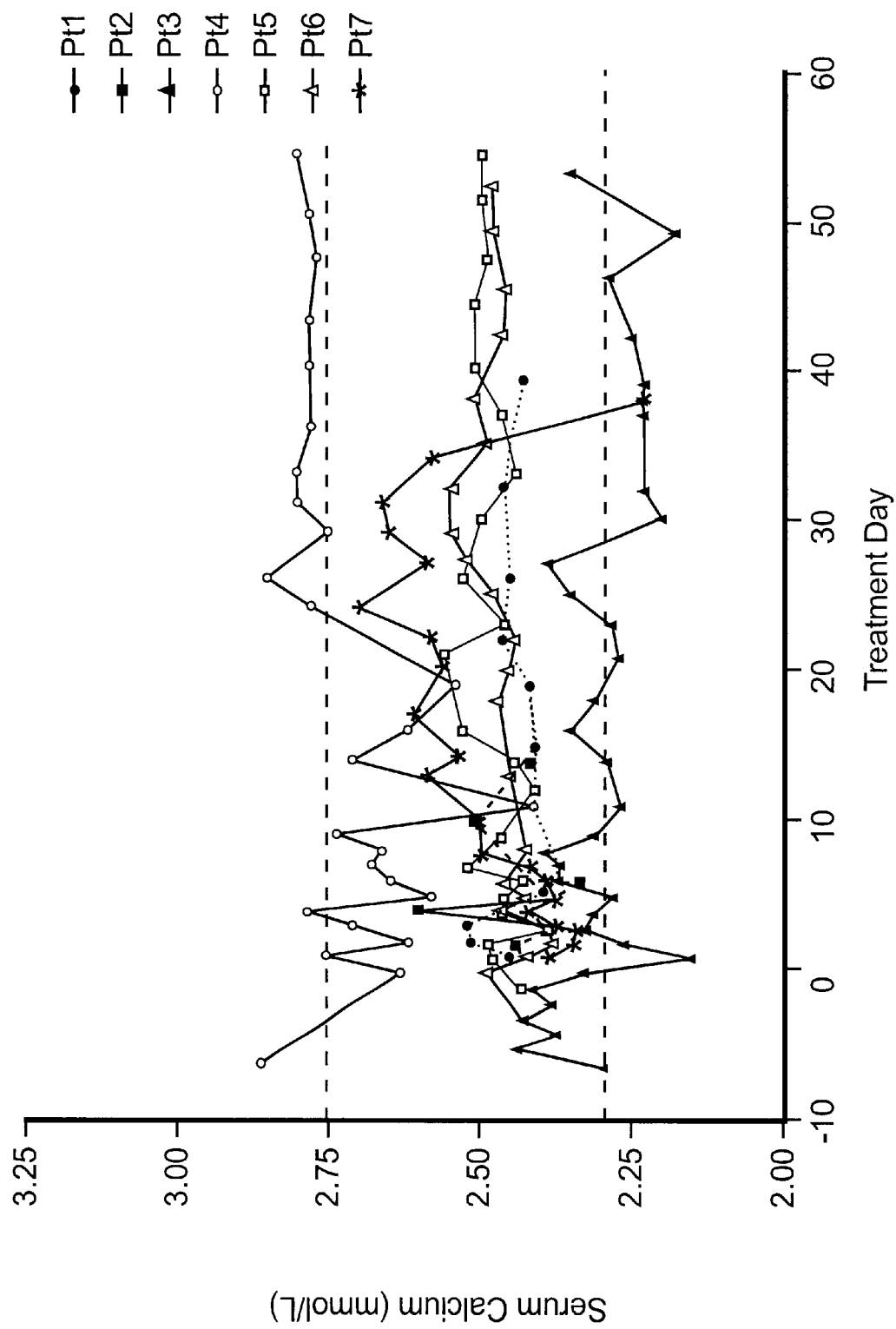
Figure 7:
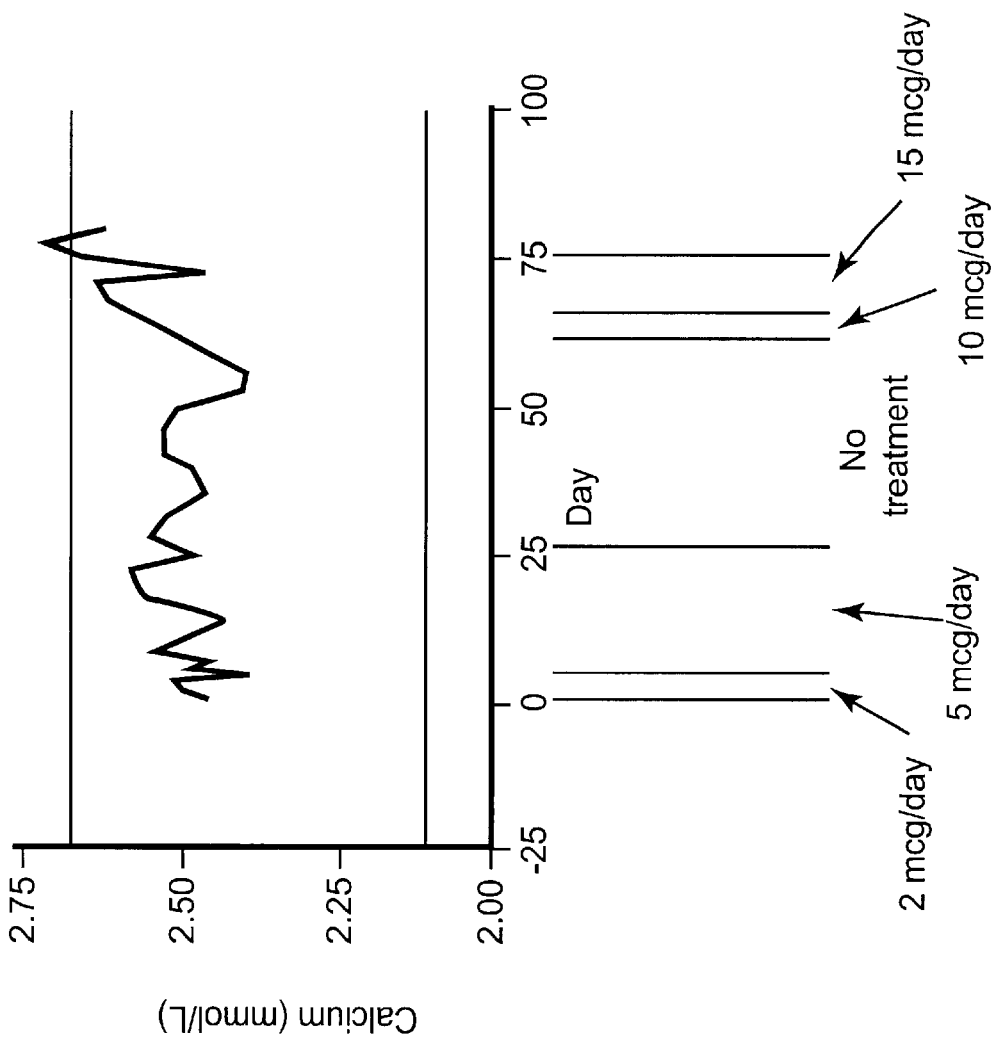

FIGS. 5, 6 and 7 demonstrate that does of up to 10 mcg/day can be administered via this route without producing hypercalcaemia. These figures also show that in two out of three patients given 15 mcg/day of 1.25(OH)$D_3$ hypercalcaemia developed.

Figure 8:
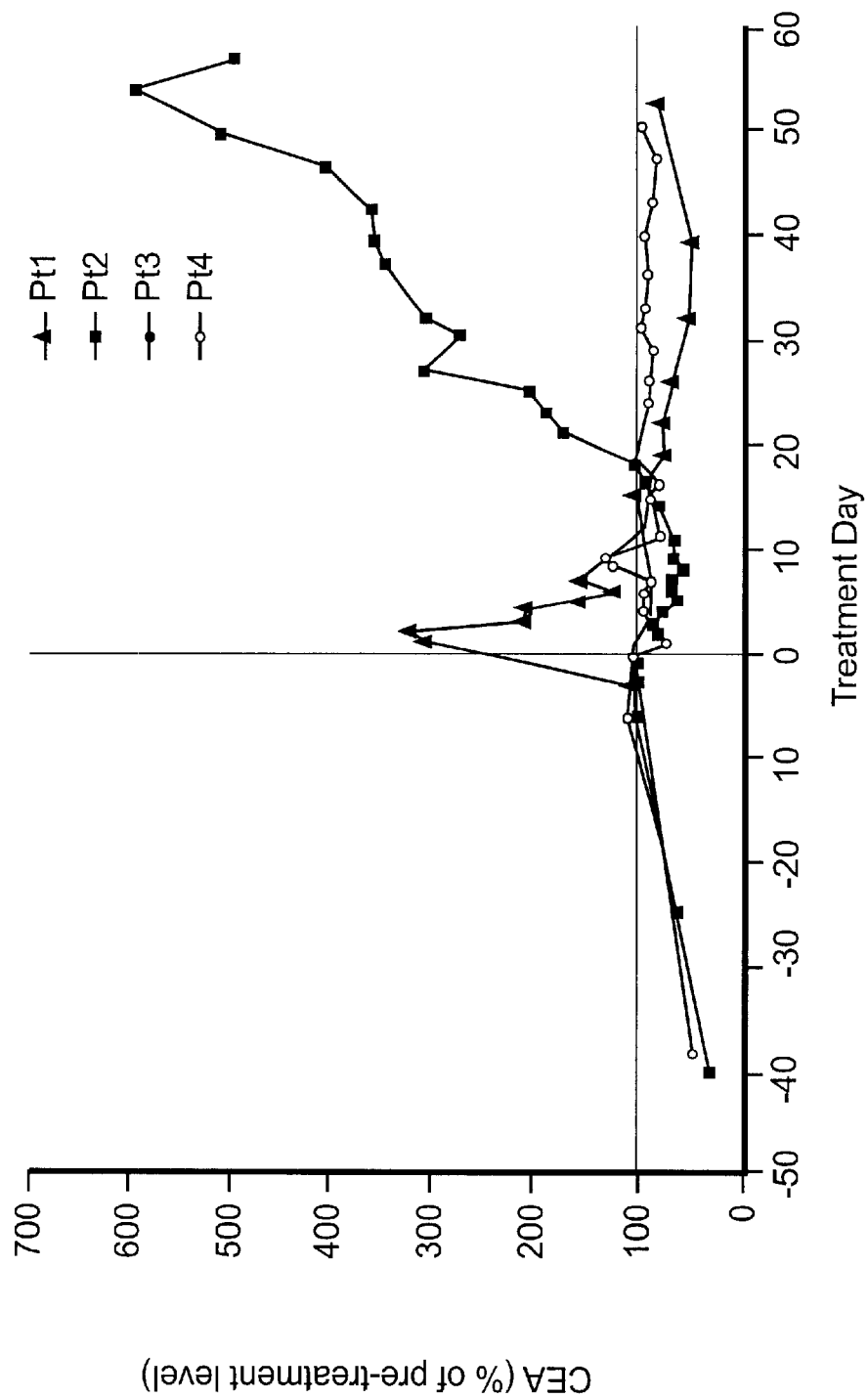
FIGS. 8–9 are graphs showing patient CEA levels during a course of treatment in accordance with the present invention.
Figure 9:
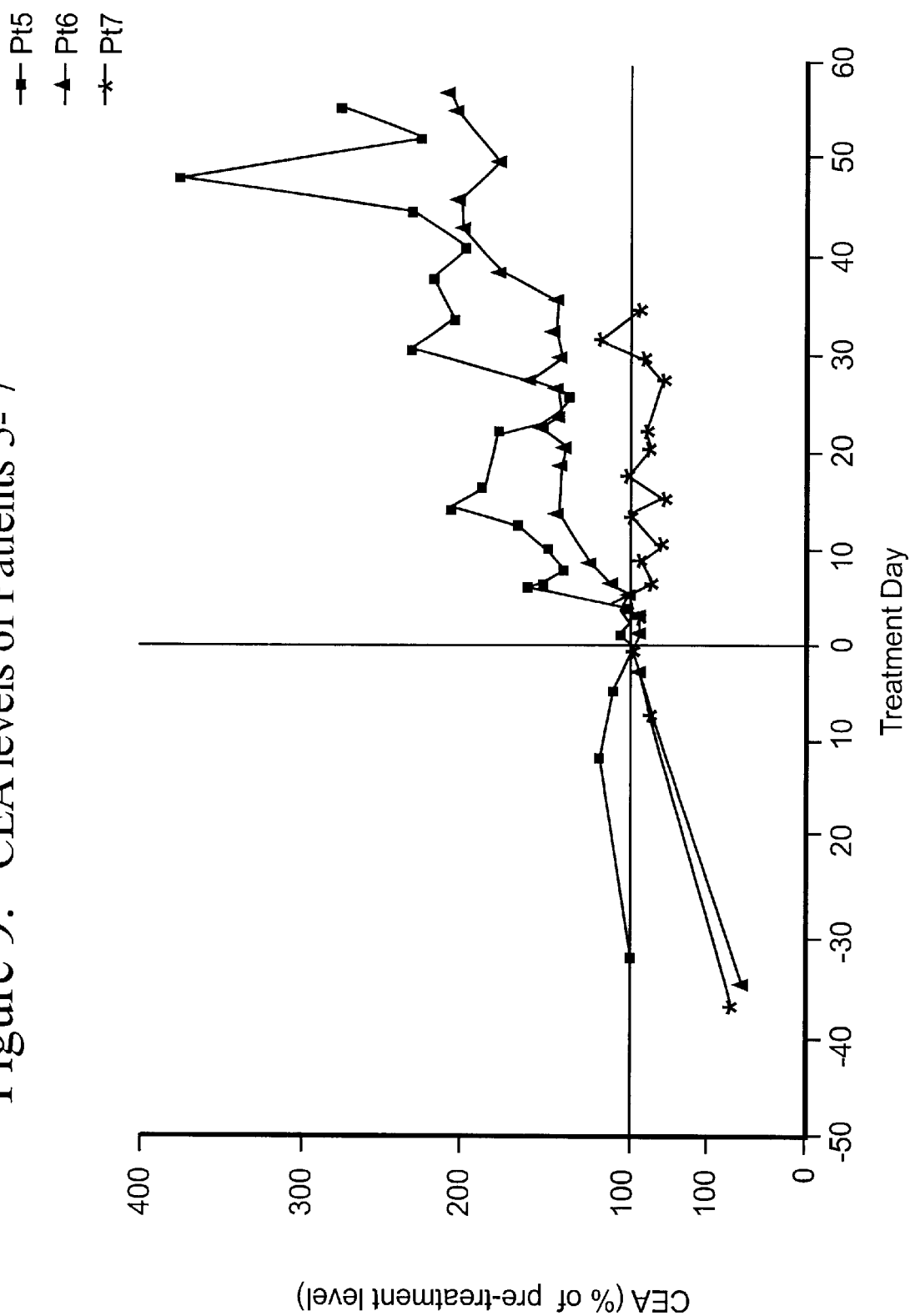

FIGS. 8 and 9 detail the tumour marker responses of all seven patients. As can be seen in FIG. 7, patient 1's marker level dramatically increased at the onset of treatment but this was followed by an equally dramatic fall in the level. Patient 2 did not experience a fall in marker level but there was a levelling off of the rate of rise with time. Patient 3 had a dramatic fall in marker level initially, but later this resumed it rise. This rise was noted to occur at the same time that extrahepatic disease was noted to have developed. FIG. 9 illustrates that patients 5 and 6 did not appear to have any response to treatment in terms of CEA levels rate of rise, however the rate of rise of CEA levels of patient 7 appears to have slowed somewhat perhaps indicating a response.

Discussion and Conclusions

We have demonstrated that the administration of 1.25 (OH)$D_3$ as an infusion via the hepatic artery is safe and without unexpected side effects. Up to 10 mcg/day of 1.25(OH)$D_3$ can be given without producing hypercalcaemia. This compares with a previous trial in which 2 mcg/day of calcitriol was administered orally and resulted in hypercalcaemia in 50% of patients.

The tumour marker data is more difficult to interpret, given the fact that these patients all had very advanced hepatic disease and extrahepatic disease to varying degrees, but it would appear that 4 of the 7 patients treated had at least a limited response to treatment as indicated by a fall in the rate of rise of their tumour marker levels with time.

Example 3

A Pig Animal Model Comparing the Effects of an Intravenous Administration of 1.25(OH)$D_3$ Versus an Intravenous Infusion Aims To investigate the existence of a first pass effect on a hepatic arterials infusion of 1.25(OH)$D_3$ by comparing such an infusion's effects upon serum calcium levels with the effects of an identical dosage intravenous infusion.

Subjects

Female Landrace pigs (minimal disease) of weight 15–50 kg.

Methods

Each animal was anaesthetised and a hepatic arterial catheter or intravenous catheter was inserted, and connected to an implanted "Infusaid" pump which delivered a continuous infusion of 1.25(OH)$D_3$. This infusion was delivered for a one or two week period, after which the animal was not treated for 4 weeks to allow any induced hepatic enzymes to diminish. The animal was then "crossed over" those whose first infusion was via the hepatic artery had their pump connected to an intravenous catheter and vice versa.

Blood was taken regularly and assayed foe calcium levels, LFTs and UECs.

Results

To date three pigs have been entered into and completed the trial. Pigs 1 and 2 have both undergone intravenous and hepatic artery infusions. Pig 3 unfortunately had a reaction to halothane anaesthesia—malignant hyperpyrexia and died at its operation. No pig suffered any unexpected reaction to 1.25(OH)$D_3$ via either route, LFTs and UECs being normal in all animals throughout.

Figure 10:
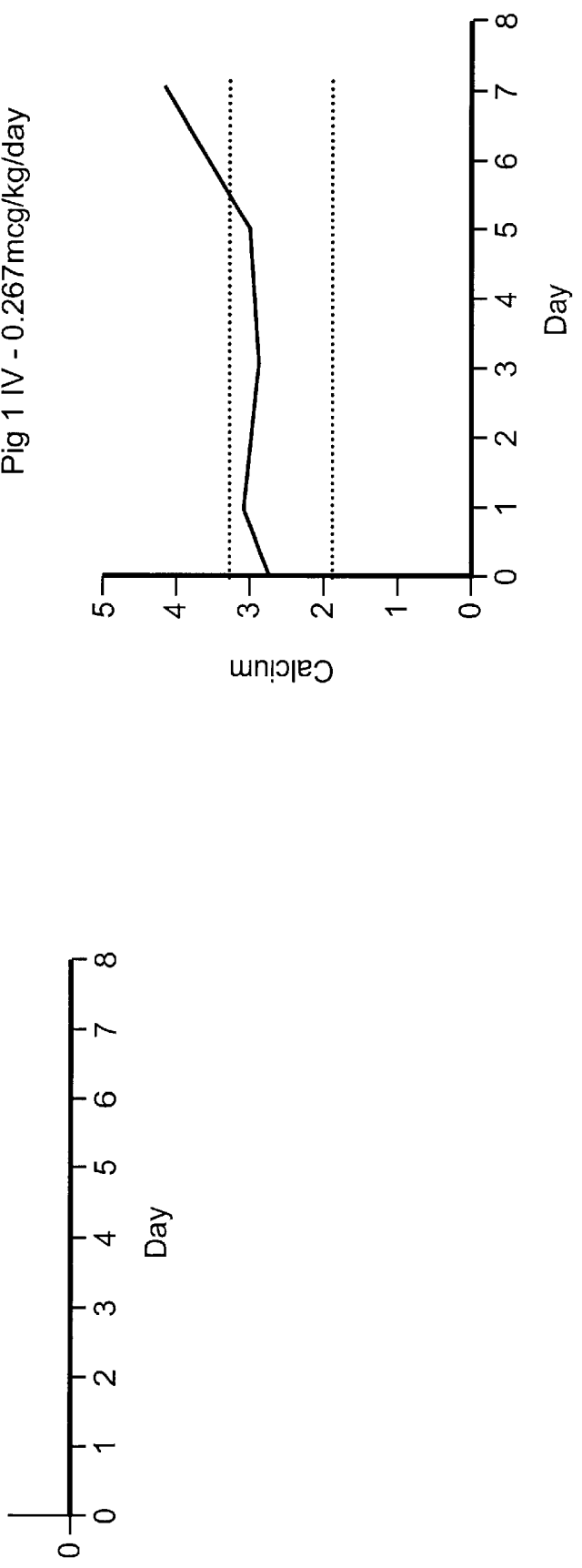
FIGS. 10–11 are charts showing calcium levels of pigs one and two respectively showing calcium 1 levels for intravenous and hepatic artery infusions.
Figure 11:
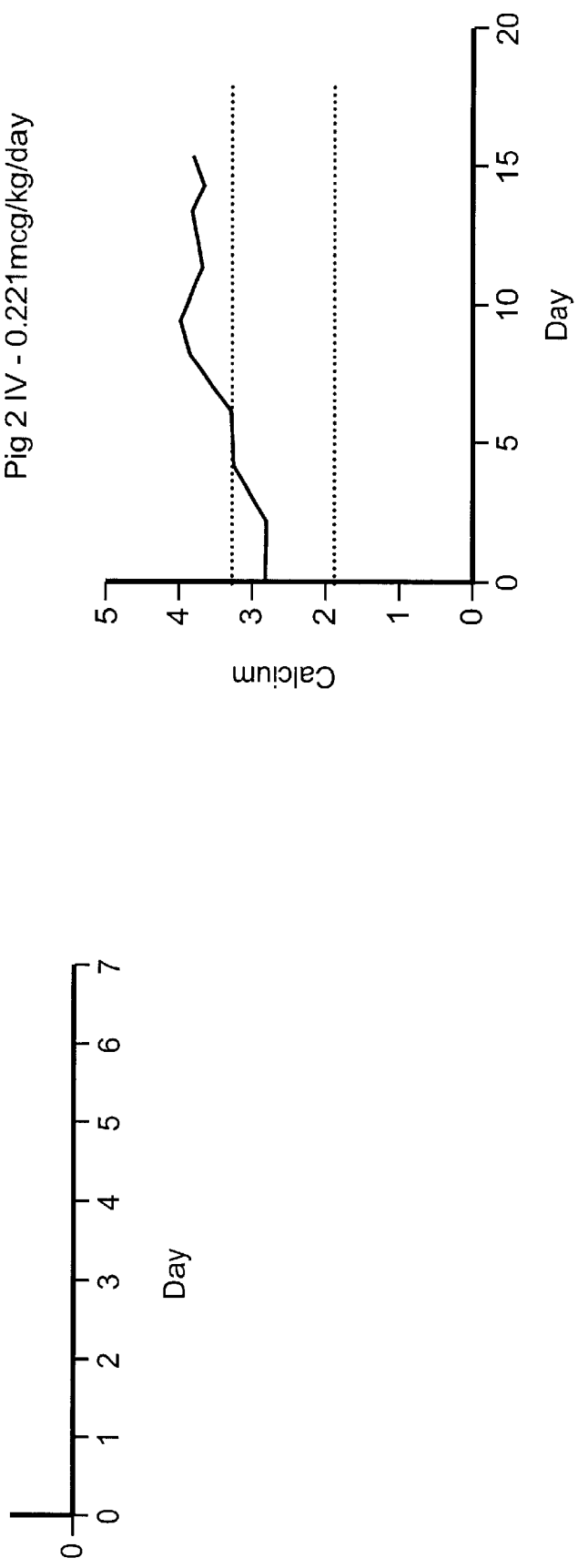

FIG. 10 illustrates the calcium levels resulting from both intravenous and hepatic arterial infusions of 1.25(OH)$D_3$. Clearly the intravenous route of delivery results in hypercalcaemia whereas a similar dosage when delivered via the hepatic artery does not affect calcium levels FIG. 11 demonstrates the similar results in pig 2 as for pig 1.

Discussion and Conclusions

This trial demonstrates that an infusion of 1.25(OH)$D_3$ delivered via the hepatic artery does not produce the hypercalcaemia seen when a similar dose is delivered intravenously. This supports the existence of a first pass effect associated with hepatic arterial infusion of 1.25(OH)$D_3$.

Example 4

Determination of Solubility of Vitamin $D_3$ in Lipiodol

Figure 12:
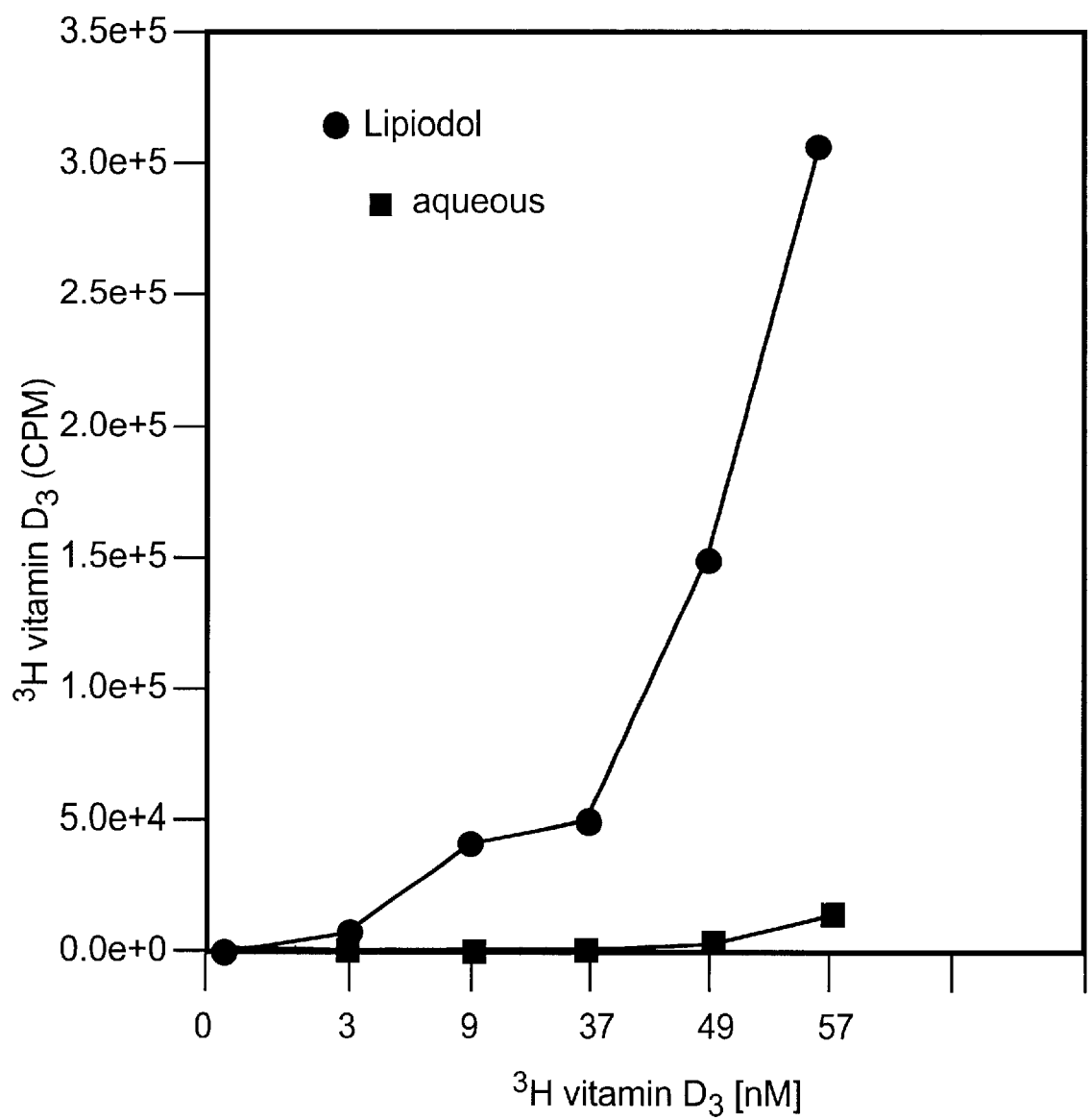
FIG. 12 is a graph showing the solubility of 3H vitamin D3 in both water and lipiodol.

To illustrate the solubility of vitamin D compound in lipiodol radiolabelled vitamin $D_3$ was dissolved in lipiodol at various amounts and the compared to the solubility of radiolabelled vitamin $D_3$. The results are shown in FIG. 12 which demonstrates that vitamin $D_3$ is substantially more soluble in lipiodol that in an aqueous medium.

It will be appreciated by persons skilled in the art that numerous variations and/or modifications may be made to the invention as shown in the specific embodiments without departing from the spirit or scope of the invention as broadly described. For example, the treatment method of the present invention may be used with one or more conventional anti-cancer therapies such as radiation therapy or chemotherapy. The present embodiments are, therefore, to be considered in all respects as illustrative and not restrictive.

What is claimed is:

1. A method of treating a tumor in the liver of a subject comprising administering to the subject a pharmaceutically effective amount of at least one vitamin D compound selected from the group consisting of vitamin $D_3$, $1.25(OH)_2 D_3$, OCT, MC903 and EB1089, wherein the vitamin D compound is regionally delivered to the liver.

2. A method according to claim 1 wherein the vitamin D compound is delivered intraarterially or via the portal vein.

3. A method according to claim 2 wherein the vitamin D compound is delivered by hepatic artery infusion.

4. A method according to claim 1 wherein the vitamin D compound is delivered in a composition containing a pharmaceutically acceptable oil.

5. A method according to claim 4 wherein the pharmaceutically acceptable oil is an iodised oil.

6. A composition according to claim 5 wherein the iodised oil is lipiodol.

7. A method according to claim 1 wherein the tumour is a primary cancer of the liver.

8. A method according to claim 7 wherein the cancer is hepatoma.

9. A method according to claim 1 wherein the tumour is a secondary cancer of the liver.

10. A method according to claim 9 wherein the cancer is a metastases of a cancer selected from the group consisting of colorectal cancer, lung cancer, breast cancer, prostate cancer, pancreatic cancer and renal cancer.

11. A method according to claim 9 wherein the secondary cancer is a sarcoma.

12. A method according to claim 1 wherein the vitamin D compound is $1.25(OH)_2D_3$.

13. A method according to claim 1 wherein the vitamin D compound is administered with a compound capable of increasing vitamin D receptor expression.

14. A method according to claim 13 wherein the compound capable of increasing vitamin D receptor expression is an oestrogen receptor antagonist.

15. A method according to claim 14 wherein the compound is tamoxifen.

16. A method according to claim 1 further including one or more other anticancer treatments.

17. A method according claim 16 wherein the other anticancer treatment is selected from radiation therapy or chemotherapy.

18. A method according to claim 1, wherein the vitamin D compound is selected from the group consisting of vitamin $D_3$, OCT, MC903 and EP1089.

* * * * *